United States Patent
Troxler, Jr. et al.

(10) Patent No.: US 10,515,731 B1
(45) Date of Patent: Dec. 24, 2019

(54) NUCLEAR GAUGE

(71) Applicant: Troxler Electronic Laboratories, Inc., Research Triangle Park, NC (US)

(72) Inventors: William F. Troxler, Jr., Raleigh, NC (US); Wewage Hiran Linus Dep, Raleigh, NC (US); Robert Ernest Troxler, Raleigh, NC (US)

(73) Assignee: Troxler Electronic Laboratories, Inc., Research Triangle Park, NC (US)

(*) Notice: Subject to any disclaimer, the term of this patent is extended or adjusted under 35 U.S.C. 154(b) by 1853 days.

(21) Appl. No.: 14/214,409

(22) Filed: Mar. 14, 2014

Related U.S. Application Data

(60) Provisional application No. 61/785,037, filed on Mar. 14, 2013.

(51) Int. Cl.
*G21F 5/02* (2006.01)

(52) U.S. Cl.
CPC ...................................... *G21F 5/02* (2013.01)

(58) Field of Classification Search
CPC .......... G01T 7/005; G01N 23/203; G21F 5/02
See application file for complete search history.

(56) References Cited

U.S. PATENT DOCUMENTS

| | | | |
|---|---|---|---|
| 4,152,600 A | 5/1979 | Berry | |
| 4,525,854 A | 6/1985 | Molbert et al. | |
| 4,641,030 A | 2/1987 | Regimand | |
| 4,743,831 A | 5/1988 | Young | |
| 4,766,319 A | 8/1988 | Regimand | |
| 4,864,842 A | 9/1989 | Regimand | |
| 4,874,950 A | 10/1989 | Regimand | |
| 4,979,197 A | 12/1990 | Troxler, Sr. et al. | |
| 5,029,194 A | 7/1991 | Young et al. | |
| RE34,070 E | 9/1992 | Regimand | |
| 5,151,601 A | 9/1992 | Regimand | |
| 5,315,124 A * | 5/1994 | Goss | G21F 5/02 250/496.1 |
| 5,532,492 A | 7/1996 | He et al. | |
| 6,310,936 B1 | 10/2001 | Troxler et al. | |
| 6,369,381 B1 | 4/2002 | Troxler et al. | |
| 6,442,232 B2 | 8/2002 | Troxler et al. | |
| 6,492,641 B1 | 12/2002 | Dep et al. | |
| 6,567,498 B1 | 5/2003 | Troxler et al. | |
| 6,617,599 B2 | 9/2003 | Weger et al. | |
| RE38,910 E | 12/2005 | Troxler et al. | |
| 7,239,150 B2 | 7/2007 | Troxler et al. | |
| 7,569,810 B1 | 8/2009 | Troxler et al. | |
| 7,605,366 B2 | 10/2009 | Dep et al. | |
| 7,705,614 B2 | 4/2010 | Troxler et al. | |
| 7,820,960 B2 | 12/2010 | Troxler et al. | |

(Continued)

*Primary Examiner* — Hugh Maupin
(74) *Attorney, Agent, or Firm* — NK Patent Law

(57) ABSTRACT

A gauge is provided for measuring one or more characteristics of a construction material such as a road surface. The gauge includes a detector, a base that carries the detector, and a source housing carried by the base and defining a shield material circumferentially extending inwards. A source rod is positioned within the housing and carries a source that is translatable between a shielded position within the housing and a measuring position external of the housing. The source rod has a source shield on the top thereof and a shield material spaced-downwardly from the source such that the source is completely enclosed when contained within the base.

15 Claims, 11 Drawing Sheets

(56) References Cited

U.S. PATENT DOCUMENTS

| | | |
|---|---|---|
| 7,848,905 B2 | 12/2010 | Troxler et al. |
| 7,872,222 B1 | 4/2011 | Troxler |
| 7,928,360 B2 | 4/2011 | Troxler |
| 8,071,937 B2 | 12/2011 | Troxler |
| 8,126,680 B2 | 2/2012 | Troxler et al. |
| 8,164,048 B2 | 4/2012 | Weger et al. |
| 8,294,084 B2 | 10/2012 | Troxler et al. |
| 8,299,808 B2 | 10/2012 | Troxler |
| 8,400,168 B2 | 3/2013 | Troxler et al. |
| 8,410,423 B2 | 4/2013 | Bartlett et al. |
| 8,428,913 B2 | 4/2013 | Troxler |
| 8,492,706 B2 | 7/2013 | Troxler |
| 8,716,650 B2 | 5/2014 | Bartlett et al. |
| 2001/0055363 A1 | 12/2001 | Troxler et al. |
| 2003/0141464 A1 | 7/2003 | Weger et al. |
| 2013/0062579 A1 | 3/2013 | Troxler |
| 2013/0226511 A1 | 8/2013 | Troxler |
| 2014/0009170 A1 | 1/2014 | Troxler |
| 2014/0096605 A1 | 4/2014 | Troxler et al. |
| 2014/0158897 A1 | 6/2014 | Troxler et al. |

\* cited by examiner

NUCLEAR GAUGE

CROSS-REFERENCE TO RELATED APPLICATIONS

This application claims priority to U.S. Provisional Patent Application No. 61/785,037, filed on Mar. 14, 2013, the entire contents of which are hereby incorporated by reference herein.

TECHNICAL FIELD

The present disclosure relates to material testing. More particularly, the present disclosure relates to a density gauge having a radioactive source and a detector for testing material density.

BACKGROUND

Measuring one or more characteristics of a construction material is important for insuring integrity of a given building project. For example, in the road construction industry, it is important to determine the density of the underlying soil surface before, during, and after layment of asphalt or concrete, and additionally for determining the density of the asphalt or concrete during the laying process. If the density is less than a desired amount, additional rolling or compacting of the soil, asphalt or concrete may be required.

There are many methods for determining the density of the road surface, however, the most efficient and accurate method for determining density has been by using a nuclear source and counting or analyzing the nuclear radiation with some type of nuclear detector. Using a nuclear source has the disadvantage of subjecting use of nuclear sources to regulatory oversight.

Conventional nuclear-based density gauges may have various disadvantages associated therewith, including shielding required to limit accidental or inadvertent exposure to the nuclear source. Accordingly, new and improved nuclear density gauges are needed.

SUMMARY

This Summary is provided to introduce a selection of concepts in a simplified form that are further described below in the Detailed Description of Illustrative Embodiments. This Summary is not intended to identify key features or essential features of the claimed subject matter, nor is it intended to be used to limit the scope of the claimed subject matter.

According to one or more embodiments disclosed herein, a gauge is provided. The gauge includes a source housing, detector, and a base that carries the source housing and detector.

According to one or more embodiments disclosed herein, the gauge includes a control mechanism by which a source is deployed.

According to one or more embodiments disclosed herein, the gauge includes planned breakage area by which the source housing is attached to the base.

According to one or more embodiments disclosed herein, the gauge includes a shielding material such as lead encased in a rugged housing including steel or tungsten.

According to one or more embodiments disclosed herein, the source has an exposure rate less than a predetermined threshold.

According to one or more embodiments disclosed herein, the gauge surface has an exposure rate less than a predetermined threshold.

According to one or more embodiments disclosed herein, the volume surrounding the gauge has an exposure rate less than a predetermined threshold.

According to one or more embodiments disclosed herein, the partial area incorporating the steradian immediate the gauge has an exposure rate less than a predetermined threshold.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed invention is not limited to the specific methods and instrumentalities disclosed. In the drawings.

DETAILED DESCRIPTIONS

While the disclosure of the technology herein is presented with sufficient details to enable one skilled in this art to practice the invention, it is not intended to limit the scope of the disclosed technology. The inventors contemplate that future technologies may facilitate additional embodiments of the presently disclosed subject matter as claimed herein. Moreover, although the term "step" may be used herein to connote different aspects of methods employed, the term should not be interpreted as implying any particular order among or between various steps herein disclosed unless and except when the order of individual steps is explicitly described.

Figure 1:
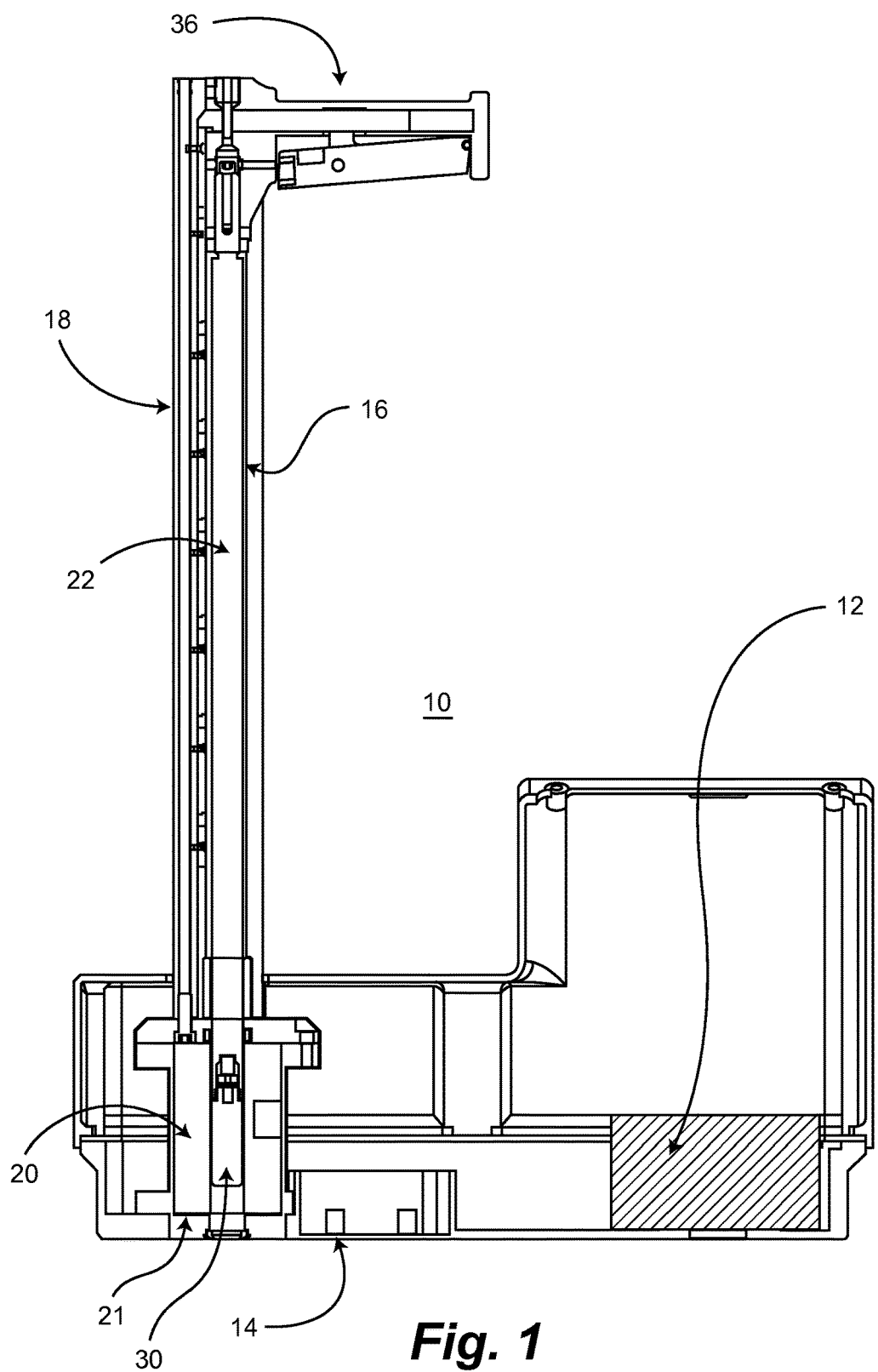
FIG. 1 illustrates a gauge for measuring one or more properties of a surface according to one or more embodiments disclosed herein.

According to one or more embodiments, a gauge is illustrated in FIG. 1 and generally designated 10. In the particular embodiment that is illustrated, the gauge 10 includes a detector 12 and a base 14 that carries the detector 12. The detector 12 may be any appropriately configured device that is able to detect one or more measurements related to a nuclear source. For example, detector 12 may be a Geiger Mueller tube, a scintillation detector, and the like.

Uses for a gauge 10 according to various embodiments described herein include but are not limited to measuring density and moisture of compacted soils, asphalt, and concrete in roadway and industrial scale parking lots. Further uses include determining moisture and density of soils, soil bases, aggregate, concrete, and asphaltic concrete without the use of core samples.

With additional reference to FIG. 1, the gauge 10 further includes a source rod housing 16 (that is carried by the base 14. The base/source housing 21 may define a shield material 20 circumferentially extending inwards. The shield material 20 may be any appropriately configured or selected material capable of shielding nuclear radiation, including, without limitation, lead, tungsten, and the like. A guide rod or enclosure 18 may be provided for guiding and indexing the source rod housing 16.

Figure 2:
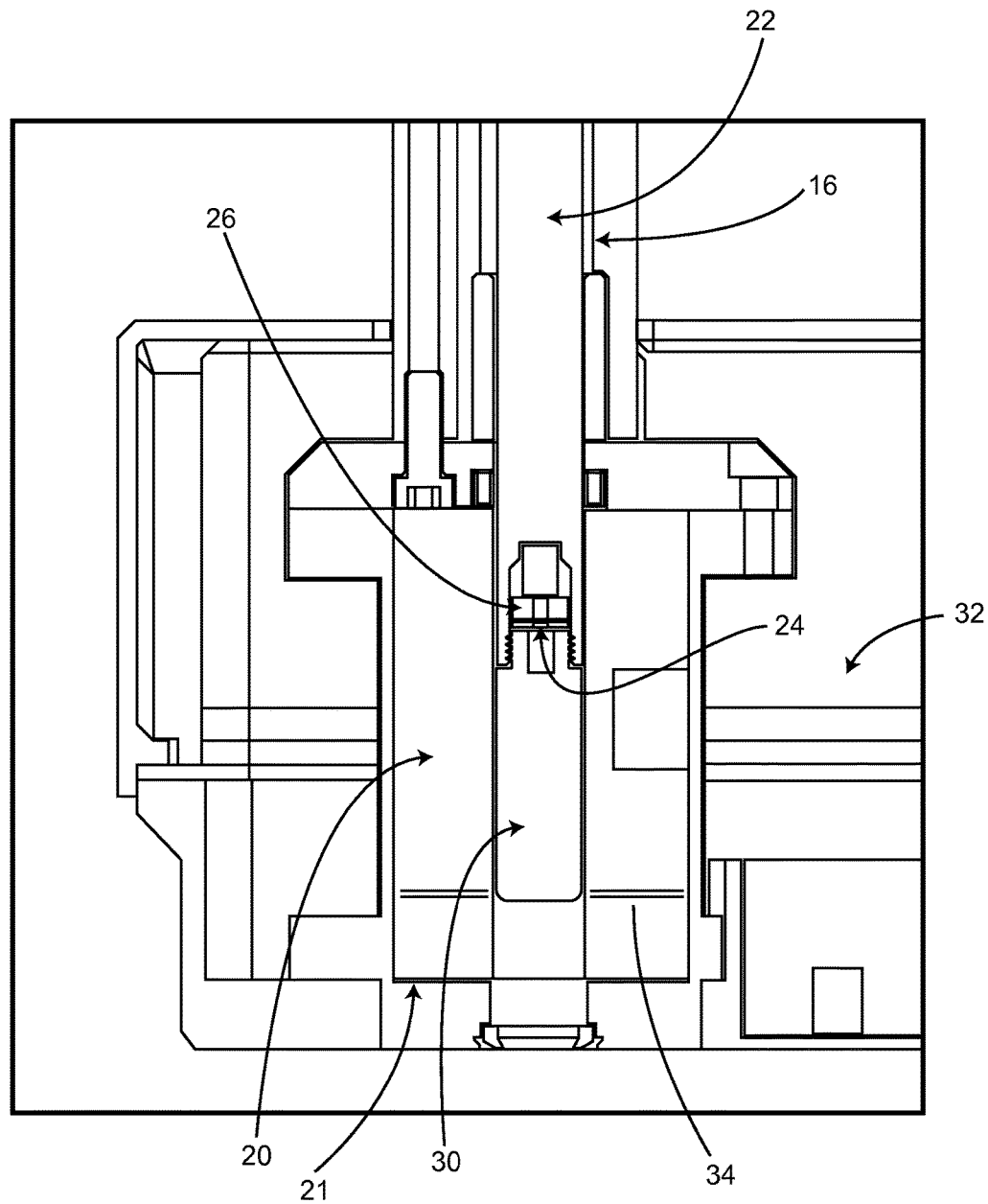
FIG. 2 illustrates a enlarged, partial view of the gauge of FIG. 1 according to one or more embodiments disclosed herein.
Figure 3:
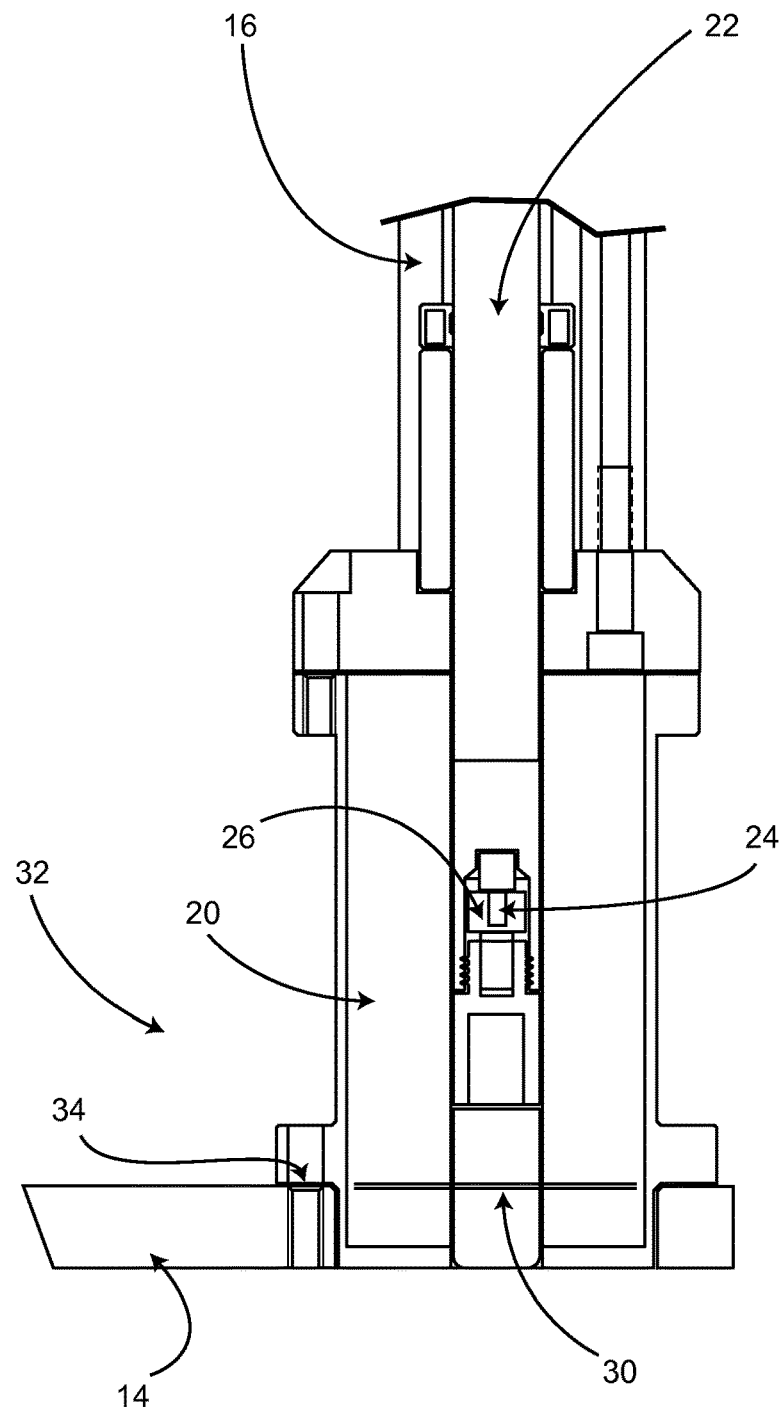
FIG. 3 illustrates a enlarged, partial view of the gauge of FIG. 1 according to one or more embodiments disclosed herein.

A source rod 22 is positioned within the source rod housing 16 in the gauge 10 illustrated in FIG. 1, FIG. 2, and FIG. 3. The source rod 22 carries a source 24 that is translatable between a shielded position within the source housing 21 and a measuring position external of and extended out of the source housing 21. The source 24 may be any appropriately configured source, such as, for example a source that contains 0.00333 GBq (0.09 mCi) of Cs-137. In that or other embodiments, Co-60 is provided as a source. Cs-137 has the advantage of a having a lower ionizing energy than that of Co-60 which has the advantage of a shorter half-life.

The source 24 may be carried within a multiple of source shields 26. The source shield 26 may be made of any appropriately shielding material, such as, for example, tungsten carbide. The source rod 22 may further include a shield material 30 spaced-downwardly from the source 24. In this manner, the source 24 is encased by a shield material in all directions when in the source housing 21, specifically, the shield material 20 enclosing around a circumference of the source 24, the source shield 26 on an upward facing portion of the source 24 and the shield material 30 on a downward facing portion of the source 24. The source 24 from the factory is also doubly encapsulated in stainless steel. There is also lead shielding in the base of the gauge 10, but this is more for isolating the detectors in the background mode, and tuning the response in the standard mode.

Figure 4:
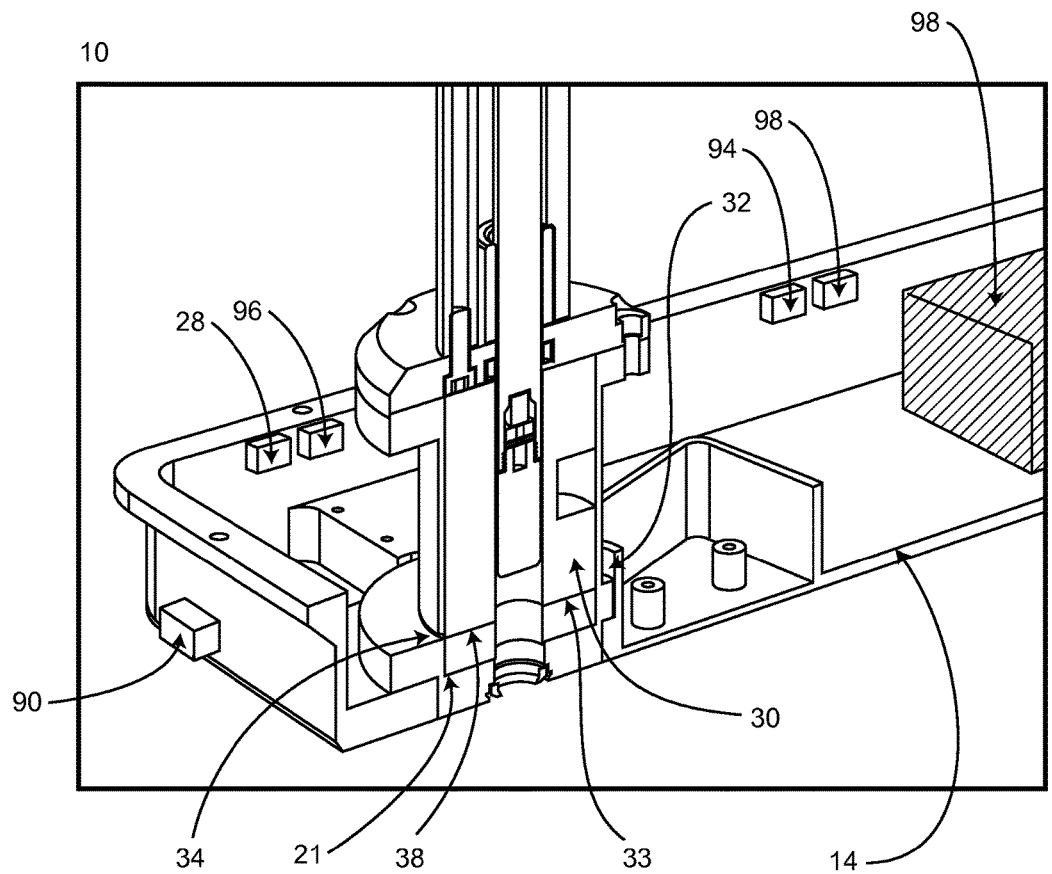
FIG. 4 illustrates a partial view of the gauge of FIG. 1 according to one or more embodiments disclosed herein.

As illustrated in FIG. 2 and with further reference to FIG. 4, the housing/tower casing 16 defines a failure zone 32 about a bottom thereof. This failure zone 32 is provided such that the base 14 separates from the source housing 21 about the failure zone 32 during an impact. In this manner, the source 24 remains in the source housing 16 and remains encapsulated in all directions by shield material 20, source shield 26, and shield material 30 when in the shielded position. As such, during a failure where the source housing 16 breaks off from the base 14, the source 24 remains entirely shielded and limits any radiation exposure that would otherwise occur. Shield material 30 may be lead, tungsten, or tungsten carbide, or any other appropriate material.

FIG. 4 shows an accelerometer 28 that may be provided, illustrated in this embodiments about base 14, for measuring acceleration of the gauge 10 in order to detect mishandling thereof. As will be discussed in further detail, the information related to acceleration may be used to provide one or more alerts to an operator, service technician, or the like.

The failure zone 32 is illustrated defining a cutout 34 that extends into the housing 16 and a corresponding cutout 38 defined in the shield material 30. In this manner, the cutout 34 provides for an area of decreased structural integrity and provides for a clean break plane of the source housing 16 about the base 14 during an impact. The cutout 34 may extend around an entire circumferential periphery of the source housing 16 as illustrated. Cutout 38 may extend entirely through shield material 30, thereby leaving a lower portion of shield material 33 that is configured to break off with the base 14. Breakaway fasteners then would connect the lower portion of the shield to the upper portion.

Though cutout 34 is illustrated as forming the failure zone, any manner of other structural, material, or other designs could be employed. For example, perforations could be provided along a circumference of the housing 16, a material could be employed in select portions having reduced structural integrity or characteristics, or some latching/unlatching structure could be provided that is configured for failure upon an impact. Failure zone could be located in the gauge base 14 instead of the tower assembly 16, so that the tower assembly 16 breaks away keeping part of the base intact with the shielding.

Examples of failure scenarios include, when the gauge 10 is on site, and a vehicle or compactor runs over it or if damage is done by other equipment, then the source 24 and shielding 20, 26 and 30 would break away from the base 14 and not separate from each other. That is, the shielding breaks away with the source 24 staying intact, thus shielding the source 24 even upon damage to the gauge 10.

By ruggedizing the tower/bioshield assembly in a configuration that, in the event of an accident, will break away from the base 14 and other portions of the gauge 10 with the tower/bioshield assembly intact to keep the source 24 shielded, safety and integrity of containment is assured. This feature has merit with regard to regulations and represents a unique design feature along with the shielding in the source rod tip to eliminate, in some embodiments, a moveable shutter or shield.

Figure 5:
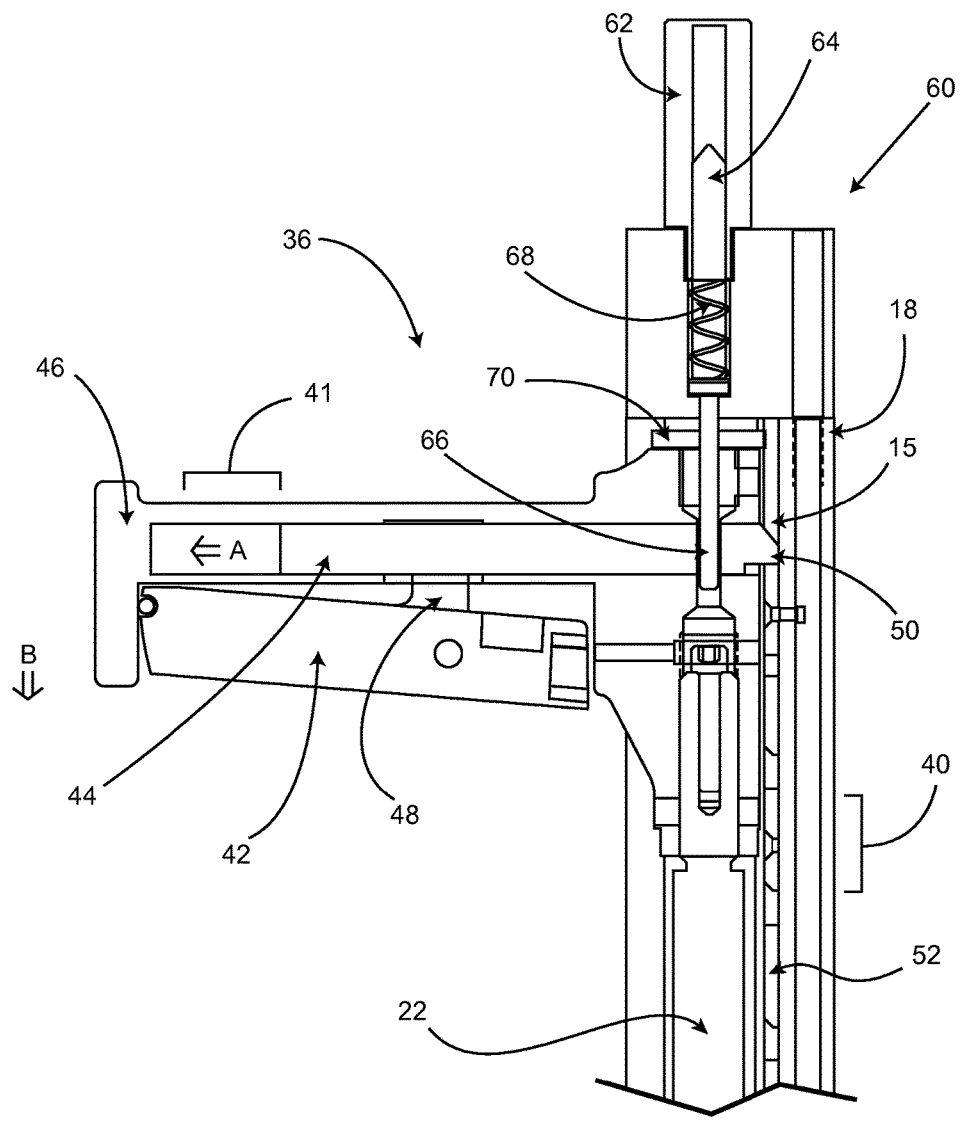
FIG. 5 illustrates a cross-sectional view of an actuator handle for actuating the gauge, where the actuator handle is in a locked position according to one or more embodiments disclosed herein.

FIG. 5 illustrates an actuator assembly 36 that is configured for translating source rod 22 so as to move the source 24 from the shielded to other positions such as the measurement position, the background and the standard position. The actuator assembly 36 may include an electronic access module 40 that must be activated in order to advance the actuator assembly 36 from the locked position to the unlocked position. The electronic access module 40 may be any appropriately configured module, such as, for example, an RFID reader that communicates with an RFID card, FOB, dongle, or the like of an authorized operator. The RFID key could be worn and use low power Bluetooth. The Bluetooth link in the user's phone could act as an automatic authorized key. In this manner, the operator must have one of the RFID card, FOB, dongle, and the like to communicate with the RFID reader in order to unlock the actuator assembly 36. Alternatively, an RFID ring to be worn by users, or a medallion, otherwise worn or carried, may unlock the source electronically.

Retracting the source to the safe position may not require a key to allow a safe configuration of the source to be implemented whether RFID access is satisfied or not. In other words, retraction back to the shielded position of source 24 does not require authentication with one or more security features disclosed herein. In this manner, in the instance where a source 24 is extended into the measuring position but later the operator does not know or does not have authentication access, the source 24 can still be retracted into the shielded position but cannot then be extended into the measuring position. A keypad is provided in some embodiments to work in conjunction with or in lieu of an RFID key. A controller executing software executable instructions may be provided.

To activate the actuator assembly 36, the trigger 42 is squeezed while gripping handle 46. This causes an arcuate profile of extension 48 of trigger 42 to impart translation of index piston 44 in the A direction arrow. A hook 50 of the index piston 44 is now spaced-apart from an index strip 52 defined on guide bar 15. With the hook 50 spaced-apart from index strip 52, the source rod 22 can be translated downwardly in the B direction arrow. A desired measurement depth is selected by releasing the handle 46 when hook 50 is proximal a corresponding index strip 52 opening. Further downward translation or return of the source rod 22 to the uppermost position may be accomplished by squeezing trigger 42, and placing the source rod 22 in a desired position. It is contemplated that although FIG. 5 shows electronic locks and authentication codes, that a mixture of mechanical locks and assemblies could be incorporated to keep unauthorized persons from exposing the source. For instance, a magnetic latch with a magnet placed at a certain spot may authenticate and allow a pin to be removed and the trigger actuated. Likewise, an allen screw (key) or latch uncovered using a keyed (key) window is also effective in unauthorized exposure of the source. Thus a double key approach.

Alternatively, in the embodiment in which an electromechanical lock assembly 60 is utilized, a solenoid 62 pushes a plunger 64 into a lock pin 66 that extends into engagement with the index piston 44. A biasing spring 68 is provided for biasing the lock pin 66 into a biased, locked state. A bushing 70 may be provided for guiding the lock pin 66.

Figure 6:
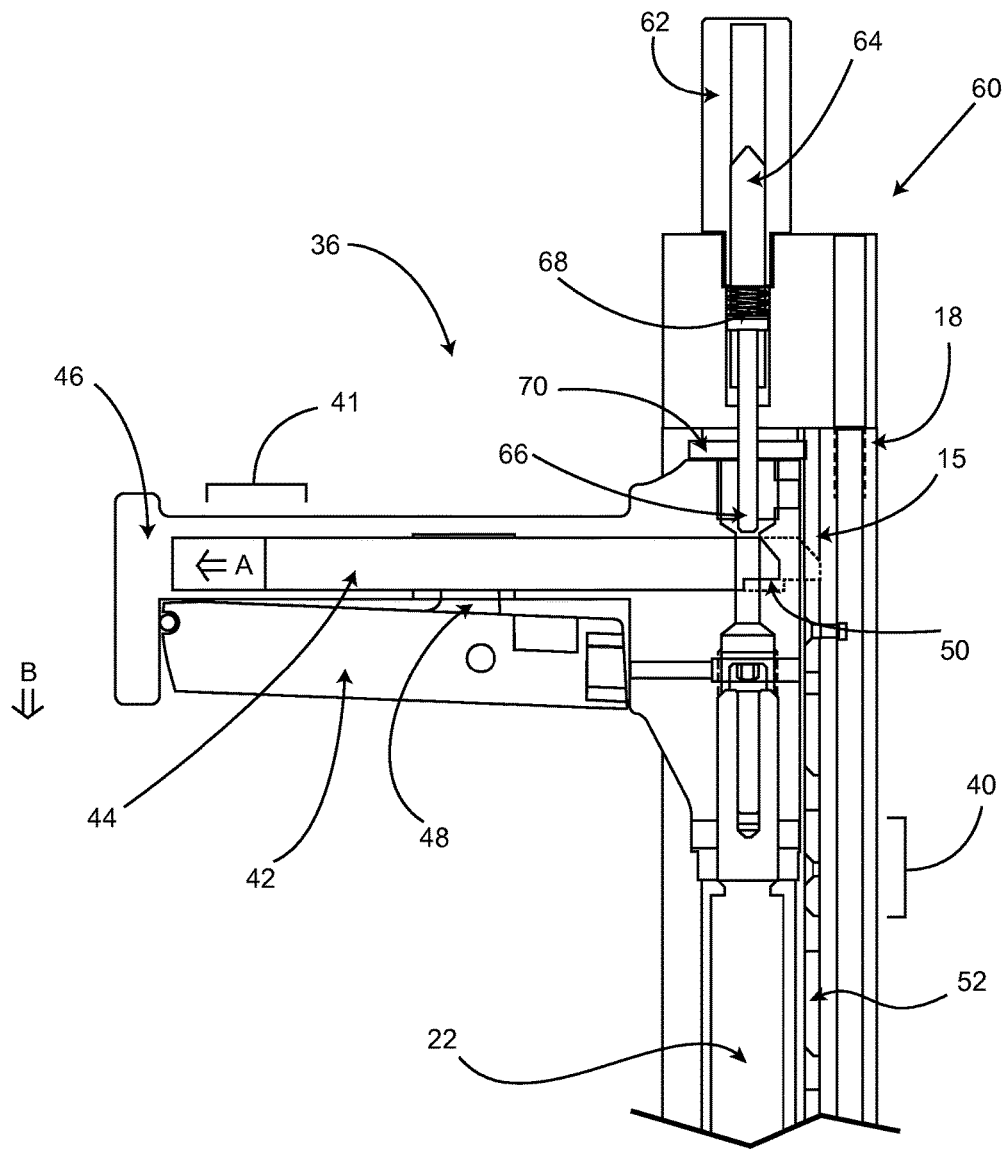
FIG. 6 illustrates a cross-sectional view of an actuator handle for actuating the gauge, where the handle has been squeezed and an index piston is shown translating towards an unlocked position according to one or more embodiments disclosed herein.
Figure 7:
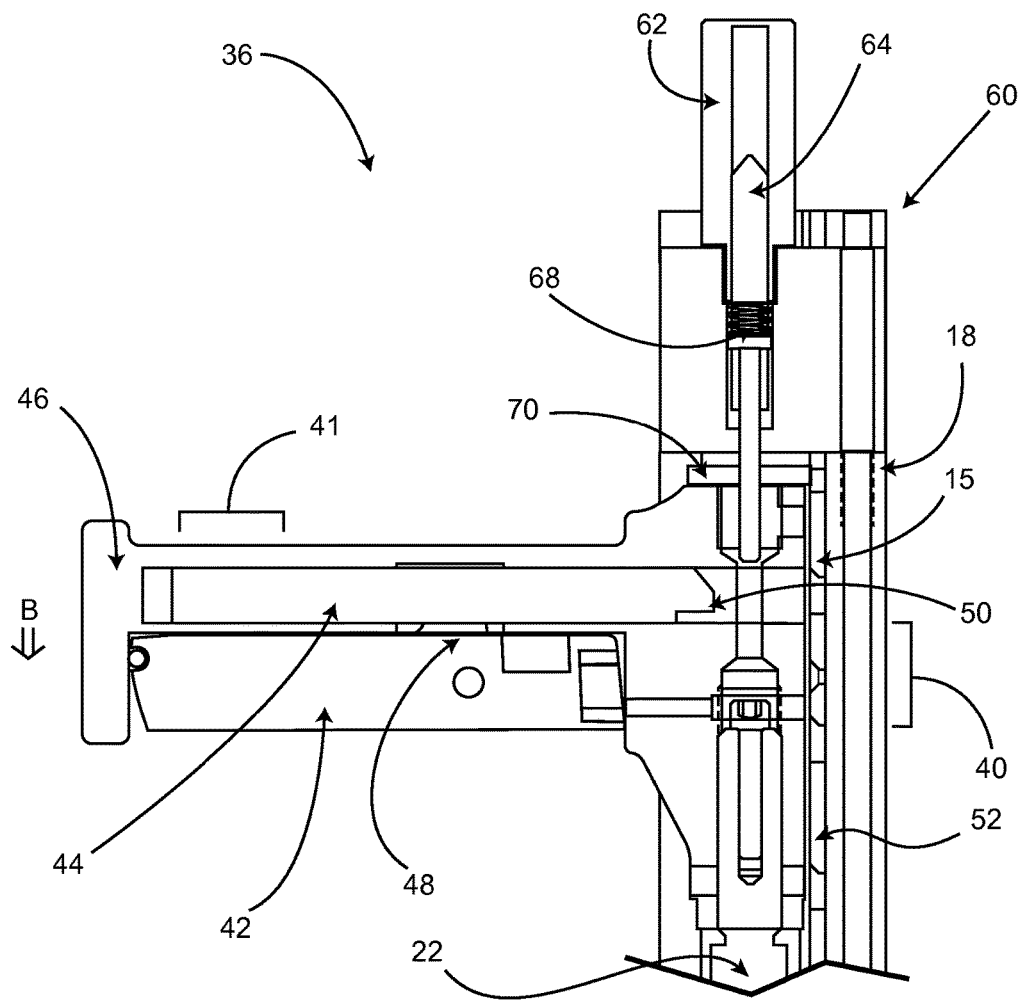
FIG. 7 illustrates a cross-sectional view of an actuator handle for actuating the gauge, where the actuator handle is in an unlocked position according to one or more embodiments disclosed herein.

The solenoid 62 is configured for being in communication with the electronic access module 40. Still, in other embodiments, a mechanical key, lock pad, and the like may be employed for actuating the spring engaged locking pin 66 Upon communication and authentication with electronic access module 40, the solenoid 62 translates the plunger 64 and lock pin 66 upwards away from the index piston 44, the trigger 42 is squeezed, and the index piston translates in the B direction arrow as illustrated in FIG. 7 such that the hook 50 is not within an index strip 52 opening and the source rod 22 can be translated along the B direction arrow by pushing downward on handle 46. Returning the source 24 to the stored/background position automatically locks the handle 46 in one or more embodiments. The pin 66 can retract back to the initial position or can be left into the unlatched position. FIG. 6 illustrates the index piston 44 translated in the direction of arrow A where the translated position is shown in solid lines and the un-translated position is shown in broken lines.

If the operator picks up the gauge 10 by grabbing onto handle 46, the handle 46 translates upwardly with the source 24 so that the gauge 10 returns to the shielded position. In one or more embodiments, an orientation detector may be utilized and in communication with the electronic access module 40 and will only allow unlocking of the actuator assembly 36 when the orientation detector 96 detects that the gauge 10 is in a horizontal, generally bottom facing downward position. In this manner, the gauge 10 cannot be turned on its side and the source 24 extended, exposing the operator to radiation. This will eliminate the ability for a user to tilt the gauge sideways to observe the source entering the hole in the ground. Other methods of lining up the source with the hole are possible, such as using a locating mat or template, pad or plate that locates the gauge directly over and aligning the source with the hole. For example, a plastic box larger than the base of the gauge is positioned over the testing hole that is 0.75 in. in diameter. A short plug of slightly smaller diameter is placed in the hole, with a "cross" frame that aligns the plastic gauge locater with the hole. Once the locater is aligned with the hole, the plug and cross are removed. Then the gauge can be placed interior to the locator with its source aligned directly over the hole. The source can then be lowered perfectly in the hole without having to tilt the gauge to the side to see the alignment. A thin pad, template, or plate could also suffice as a template. A braded holed eyelet slightly greater in diameter than 0.75 in could locate the source hole, and the thin template has an outline of the gauge. The method here would be to place the template on the predrilled hole, and flatten the thin template to the soil. Then the gauge would be placed on its outline ensuring that the source was aligned.

Still in other embodiments such as in FIG. 6, an electromechanical or electromagnetic lock assembly 41 may be included and positioned about any part of the actuator assembly 36. In one embodiment illustrated, the electromagnetic lock assembly 41 is positioned about an index piston 44 and in communication with the electronic access module 40. The electromagnetic lock assembly 41 produces an electromagnetic force against index piston 44 and maintains the index piston 44 into place until an authorized operator communicates with the electronic access module 40. In this manner, the electromagnetic lock assembly 41 prevents unauthorized use of the gauge 10 by limiting operation of the actuator assembly 36 and maintaining the source 24 in the shielded position within the source housing 16.

Figure 8:
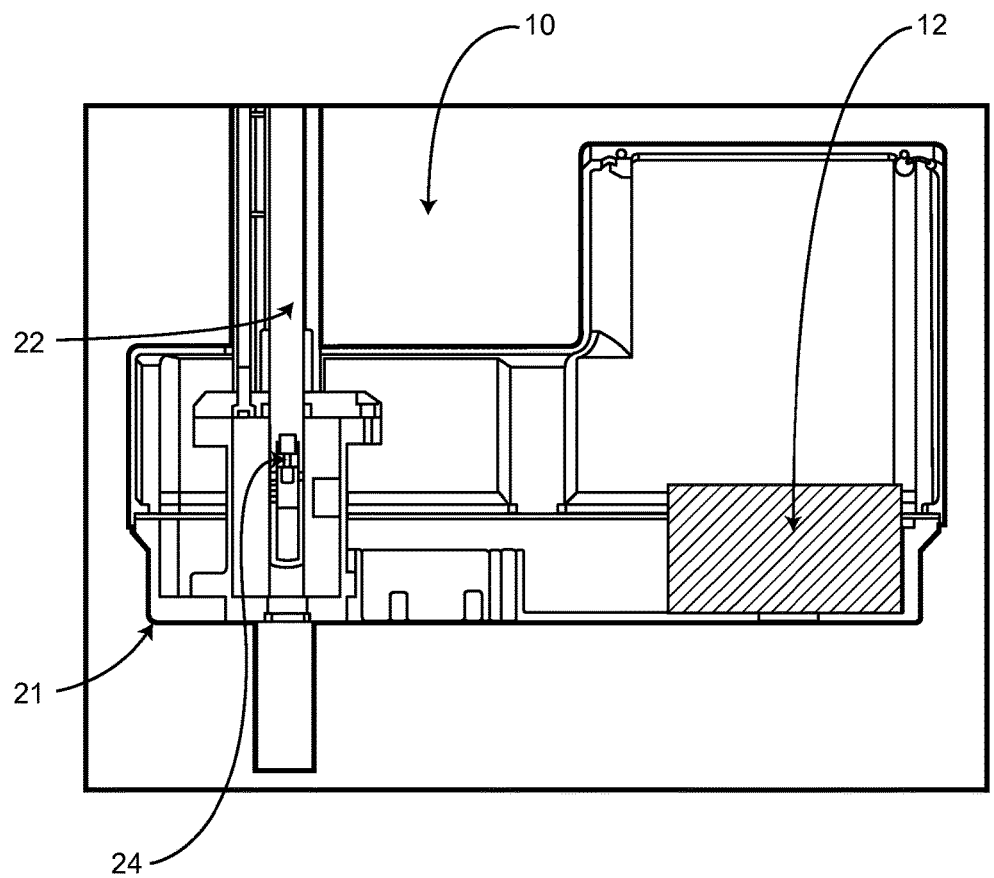
FIG. 8 illustrates a side view of the gauge positioned about a hole formed in a construction surface according to one or more embodiments disclosed herein.
Figure 9:
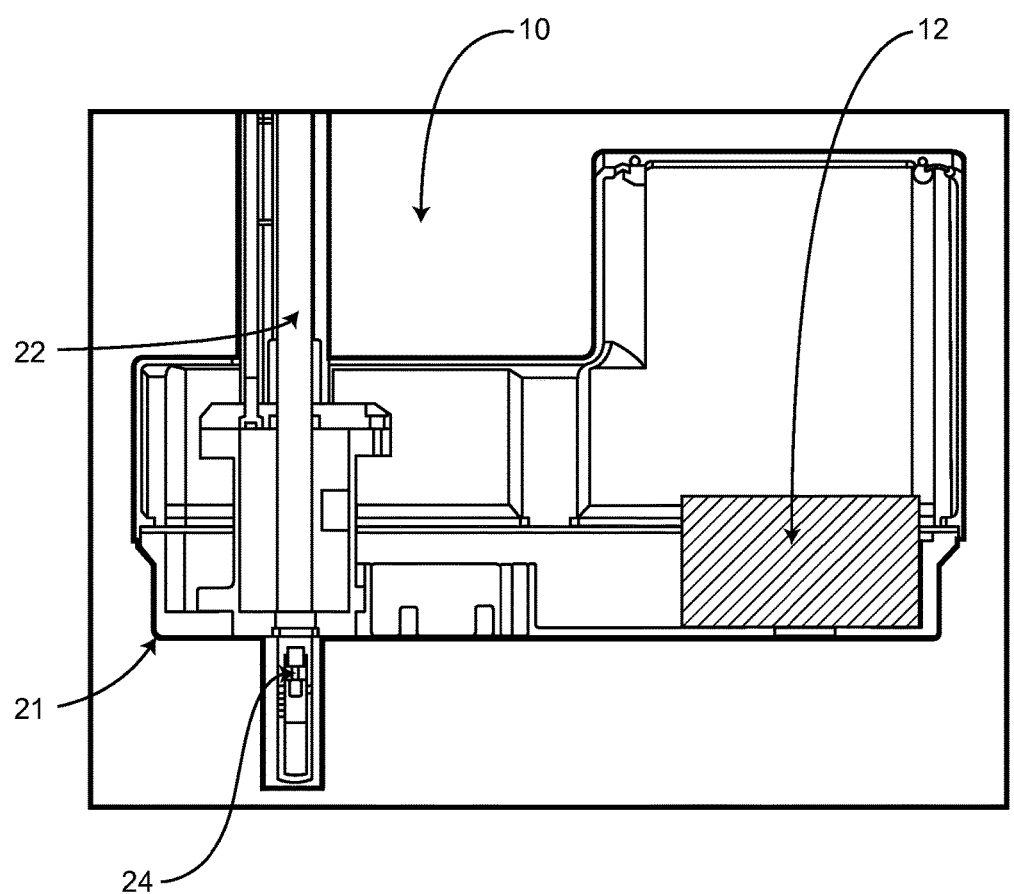
FIG. 9 illustrates a side view of the gauge where the source has been extended into the hole as illustrated in FIG. 8 according to one or more embodiments disclosed herein.

FIG. 8 and FIG. 9 illustrate placement and use of the gauge 10. A hole 80 is bored into a surface, such as a soil or sub-base surface or surface to which asphalt or concrete top layer is about to be constructed. The operator uses a template to mark or locate the position of the gauge relative to the hole 80 and then places the gauge 10 such that the source rod 22 is directly above the hole. A looking glass, visual port or similar may be provided on a portion of the gauge 10 to additionally help with this alignment or location of source in the hole. Once the gauge 10 is correctly in place, the source rod 22 is translated into the measuring position by actuating the actuator 36 as discussed with reference to FIG. 5, FIG. 6, and FIG. 7. Source rod 22 is translated into the "background" position (FIG. 8) where the "shielded" tip of the source rod is only extend out of the base 14. In this position the shielding material placed on the base 14 shields the gamma radiation reaching the detector. The gamma-radiation that is counted is correlated to the natural gamma-radiation emitted by the soil, asphalt, or concrete. A measurement of the natural gamma-radiation is required when using low activity gamma-radiation sources. FIG. 9 shows the source rod in a 'measurement' position. Measurements are then received by the detector 12 and any other characteristics that should be monitored such as location, time, authentication, and orientation detector. The measurement process may occur over a defined period of time in order to get a significant number of measurement counts.

Figure 10:
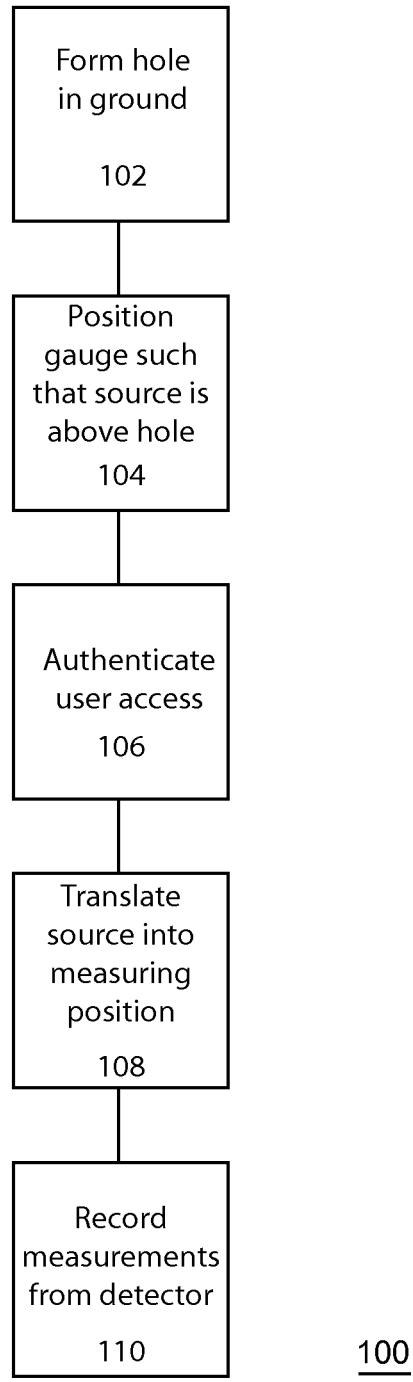
FIG. 10 illustrates a flow chart containing one or more methods according to one or more embodiments disclosed herein.

One or more methods are illustrated in the flow chart in FIG. 10 and generally designated 100. The one or more methods 100 include forming a hole in a ground or road surface 102, positioning the gauge such that the source and hole are aligned 104, this may incorporate a locating pad or device, authenticating user access by one or more authentication methods 106, translating the source into a measuring position 108, and recording, analyzing and displaying measurements from the detector 110. The authentication step may be any of the security methods disclosed herein, such as, for example, use of the access control module 40 described herein.

In one or more embodiments, the method 100 may include:
1) Prepare the test site. Level soil with scraper plate and drill or punch hole at least 2 inches deep
2) Place gauge on the site with respect to hole using gauge positioning template, locating pad or plate
3) Keep source rod in SAFE (shielded) position
4) Take a standard count by pressing STD key
5) Follow instructions on display
   message-1: "count accepted. Place the source rod to BGD position and press ENTER key"
   message-2: "count not accepted: retake count"
   message-3: "count not accepted: Move source rod to SAFE position and retake count"
   <pressing ESC key takes to the ready screen.>
6) For message-1 (count is accepted), move source rod to BGD position
7) Press ENTER key
8) Now gauge will check whether the source rod is in BGD position and take a BGD count.
   If source rod is not in BGD position, gauge displays message-1: "Place the source rod to BGD position and press ENTER key"
9) Now gauge will check whether the new standard count follows the decay trend and display
   message-1: "New standard count accepted"
   message-2: "New standard count x % different than the expected count. Do you want to accept the new count? Yes/No"
10) If count is acceptable, the gauge
   a) determines the 'Active Standard Count'
   b) assigns filenames and archives SAFE and BGD spectra
   c) displays filenames of SAFE and BGD spectra
   d) store the 'Active Background Count'

Normal operations include taking a daily standard count by drilling a hole at least 2 inches deep into a surface. In the step of forming a hole, the hole is drilled into the test material at least 1 inch deeper than the desired measurement depth. The gauge is placed over the test hole (using the template), with the source rod generally vertically aligned over the test hole. The source rod is extended into the test hole for measurement of the host material.

According to FIG. 10, access to the source 24 is restricted by safety features and modules. The source rod 22 is contained within the source rod housing 21 using security fasteners, which the typical user would not have access to. The source rod 22 may be constructed primarily of stainless steel. The end cap 26 may be constructed of stainless steel with a tungsten insert or gamma-ray absorbing insert such as lead. The source 24 is placed into the end cap 26 and the end cap 26 is permanently attached to the source rod 22 by welding for example. The interrogator system 94 may then communicate with the accelerometer 28 to determine that an impact event that could lead to failure has or has not occurred.

In one or more embodiments, in the option of using a regular sliding bioshield material, an electronic alarm system to interrogate the shield integrity is desired. This alarm system could be a mechanical switch, magnetic sensor, optical, electronic, proximity, radiation leak detector as example. The interrogator system 94 integrated into the carrying case or base 14 could also be deployed. The interrogator system 94 could interrogate the shield integrity by radiation signature, acoustic signature, electric and magnetic field sensors, proximity sensors. For example, a simple capacitive sensor can detect if the source rod 22 is in its exact position for storage. If the source 24 is removed or has mechanical problems, that would translate into a different location that could be detected by the electronic circuitry. This type of system would be used for a backscatter gauge, where the bottom shield 30 is significantly shortened or eliminated.

Diagnostics capabilities in various embodiments are included, for example to monitor the condition of the source, even when un-attended. Control/monitoring module 202 may be provided for addressing these diagnostic capabilities. A gauge controller may execute diagnostic routines in this case. If the source level becomes too large or too small, authorities could be notified. An alarm could be provided or transmitted by wireless communication, wired communication, audible report, or visual indication. Other diagnostic devices may include monitors for charging, voltage, source monitoring, count monitoring, source rod position monitoring, and temperature monitoring. A gauge position sensor may require a condition that precludes extending the source rod into air. The orientation detector 96 may be provided, and may be in communication or integrated with a locking device to assure an upright position of the gauge before permitting the source to be deployed. Diagnostic alarms could be transmitted by WiFi, Bluetooth, or cellular link.

The accelerometer 28 may be provided to record shock/stress data. Such data can be used to monitor gauge handling conditions, particularly for example to confirm mishandling or characterize handling conditions in the event of damage to the detector crystal (for example, for warranty purposes).

Other capabilities and features include: an on-board GPS device 98 for tracking of the gauge and an electronic lockout feature if the gauge is not returned to authorized personnel or facilities for safety inspection and gauge calibration occasionally, for example at predetermined intervals. A tethered source and source rod would require breaking the tether and activating an alarm. Such alarm could be audible or a communication alarm and could be triggered by voltage and current measurements of the tethered rod.

In at least one embodiment, a source view port is provided to help overcome difficulties that sometimes occur in getting the source rod to slide into the test hole. In some cases, a user considers exposing the source rod to assure alignment and insertion into the test hole. An optical view port may be provided to permit the user to visually confirm source rod alignment with the test hole. A leaded glass or lens could be used to cut down on radiation exposure from the visual port. Natural light entry is permitted in some examples. An LED or other light emitting device can be included to illuminate the area under the gauge and around the test hole. A small camera is included in some embodiments to facilitate viewing of the source and test hole. The display could be on the gauge screen, or wirelessly linked to an alternative display such as a cell phone. Alternatively, a template may be used to determine proper placement of the gauge 10.

A moisture measurement system 90 is provided in some embodiments. In particular embodiments, a non-nuclear moisture sensor is attached external to the gauge 10, with an attaching mechanism in the left or right side of the gauge base. Integrated moisture sensors are also considered. Cables for the non-nuclear sensor exit and extend from the interior of the gauge through a port in the gauge cover. The non nuclear sensor eliminates the need for a neutron emitting source, however a small neutron source may be permitted. In this matter, replacing the neutron with an electromagnetic moisture or non nuclear moisture system reduces the radioisotope configuration greatly. Examples of non nuclear moisture systems include capacitance, microwave, reflectance measurements, monopole, down hole, surface, chemical and thermal. Moisture data is transferred to the gauge controller by wire or wirelessly. Super sensitive detectors such as scintillation detectors are very efficient at reducing the gamma ray sources while keeping the standard deviation well above acceptable levels. As such, the counting statistics of these systems is substantially the same as conventional gauges with 8mCi Cs-137 gamma sources and gas Geiger Mueller tubes.

In one example, a non-nuclear moisture sensor is attached externally to the gauge, with an attaching mechanism in the left side of the gauge base. This system could also be integrated into or with the gauge 10 such as directly on the bottom. Exemplary non-nuclear moisture sensors include a fringing field capacitance device on the bottom surface, a monopole, a dipole, microwave resonator, integrated into the drill rod, or based on radar principles such as GPR, impulse radar, FMCW radar. Sensors could be ground coupled or non-contacting. Cables for Non-nuclear sensor leave the interior of the gauge through ports on the gauge outer shell.

In one or more embodiments, the source 24 is in a doubly encapsulated source capsule, which may be placed with a spring and spacer into a third capsule, which is screwed or pressed onto the Stainless Steel source rod, and then welded into place. The NRC requires that the source 24 in hand not cause greater exposure than a threshold. The third encapsulation permits higher activity to fall within regulatory standards. Previously, double-encapsulated sources were transported then further encapsulated when assembled with a source rod. According to embodiments described herein, a triple-encapsulated source is assembled permanently sealed, and transported.

According to one or more embodiments, one or more aspects that may have already been disclosed such as a GPS tracking system, automatic locking system, or even CO-60 which has a 5.26 year half life (Cs-137 has a 30 year half life) may be employed. 60 uCi will be reduced to 30 uCi after 5 years and still have 30 times more than the exempt quantity; whereas cesium would take 30 to 60 years and 80 uCi will be reduced to 40 uCi after 30 years and still have 4 times more than the exempt quantity.

The one or more embodiments herein may lead to a few manufacturing processes. Examples might be robotic welding of the source rods, source storage methods and in house procedures from shipping in to assembly, monitoring storage areas and areas where the source is handled etc.

Regarding storage of multiple gauges and concerns there toward total activity and exposure, a storage alarm could be included whereby radiation background is measured. If it gets above some set point, an alarm or notification is executed. The alarm could be the gauges as well since they have detectors in them and communication modules as an option. A gauge could wake up and do a count, even when in a shipping container in storage. An extra detector and electronics system could be incorporated into the shipping container for constant monitoring.

In one or more embodiments, the source 24 may be provided with a triple encapsulation, or quadruple encapsulation using the source rod tip as the final welded assembly. Here, the source vendor would sell the complete source rod as an entire length, which may be 14 inches long. Then the dose would be from the source rod tip, and would be much less, but at a better rate for instrument precision and background correction. At that point, the source 24 could be much bigger because of the added protection of a third or fourth layer of steel. The one or more embodiments may be accomplished as a second or even first encapsulation. Alternatively, this could be replicated at the second or even first encapsulation step with proper design and corporation. Hence, the final encapsulation could take on the form being defined as a first, second or third encapsulation. The length or dimensions of the encapsulation may not be important, just the final dose rate by definition. By triple encapsulation of the proper shielding materials, and forming a window for a highly directional radiation source, a greater amount of energetic photons from a larger source could be directed to the detector while satisfying any regulatory objectives. The overall radiation profile would be reduced, yet performance increased.

Figure 11:
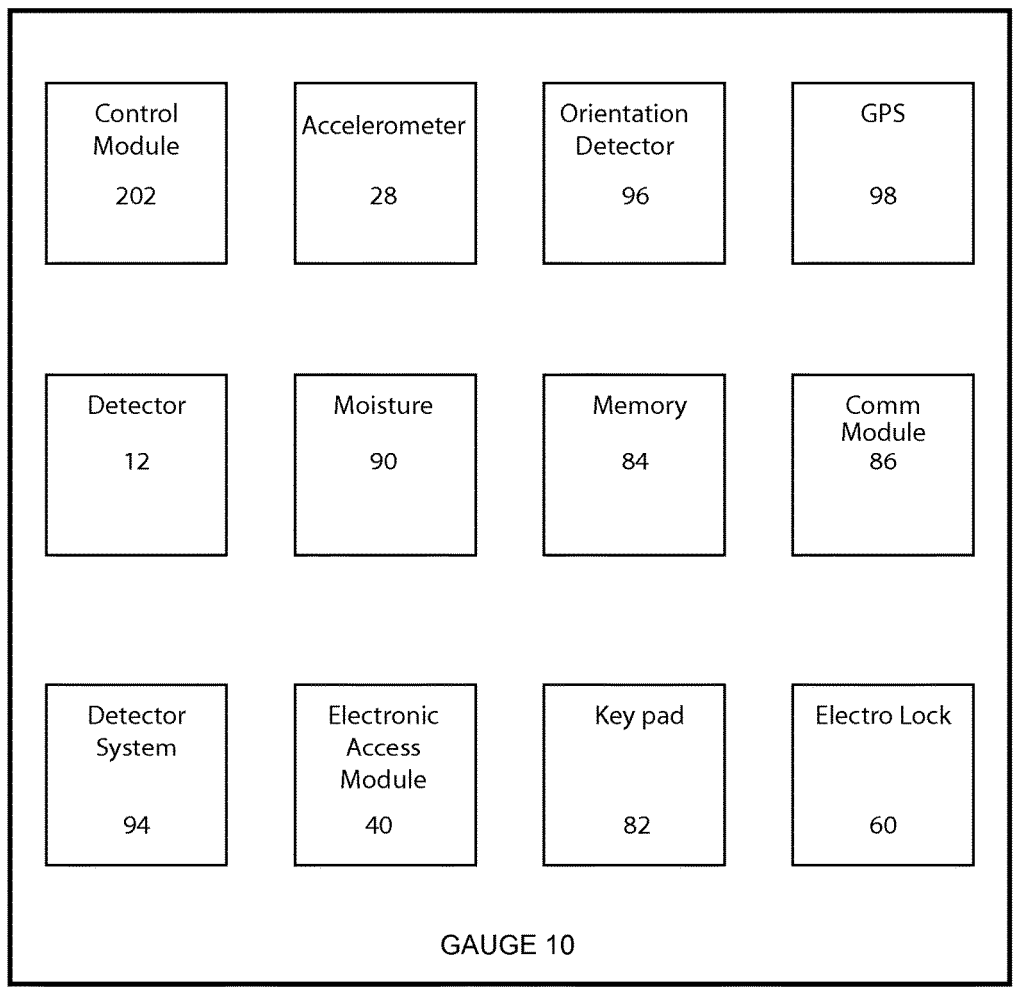
FIG. 11 illustrates a system diagram of the one or more components disclosed herein according to one or more embodiments disclosed herein.

A system is illustrated in the system diagram of FIG. 11 and generally designated 200. The system 200 is embodied on the gauge 10 and includes a control module 202 that is configured to communicate with one or more modules and aspects disclosed herein. The system 200 may be in communication with the detector 12 and monitors and stores one or more measurements found thereon onto a memory 84. Memory 84 may be ROM, RAM, or any other appropriately configured memory. A communication module 86 may also be provided and is configured for wired or wireless communication with a computer, server, or the like. The control module 202 may be in communication with the accelerometer 28. In this manner, when the control module 202 and accelerometer 28 detect an acceleration of the gauge 10 above a predetermined threshold, the control module 202 may determine that an event has occurred that could compromise the integrity of the source 24. The control module 202 may then direct the detector system 94 to interrogate the source 24 and associated shielding to determine if a compromise of the source or shielding has occurred.

The system 200 may further include a moisture sensor 90 to eliminate the need for a neutron source or may be used in combination with the neutron source or gamma source 24 in order to determine additional construction property characteristics. In this manner, both neutron related and moisture related characteristics could be determined.

The system 200 may further include an orientation detector 96. The orientation detector 96 may be any appropriately configured detector and may be in communication with the authentication module 40 and the electromagnetic lock 60. In this manner, when the control module 202 determines that the orientation detector 96 does not detect a generally horizontal position of gauge 10, the control module 202 can direct the electromechanical lock 60 to lock the source rod 22 such that the source 24 remains in the stored position.

The control module 202 may be in communication with the GPS capability module 98 and may be configured to transmit location, time, and other desired characteristics.

Additionally, a keypad 82 may be provided for communication with the authentication module 40 and any other device to which an input may be desired.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A gauge comprising:
    a detector;
    a base that carries the detector;
    a source housing carried by the base and defining a shield material circumferentially extending inwards; and
    a source rod positioned within the housing and carrying a source that is translatable between a shielded position within the housing and a measuring position external of the housing, the source rod having a source shield on the top thereof and a shield material positioned-downwardly from the source such that the source is encapsulated when in the shielded position,
    wherein the housing defines a failure zone about a bottom thereof, such that in a failure where the base separates from the source housing, the source remains shielded within the source housing.

2. The gauge according to claim 1, wherein the failure zone defines a circumferentially extending recess along the circumference of the source housing.

3. The gauge according to claim 1, wherein the failure zone is defined at a portion of the housing that is downward of an end of the source.

4. The gauge according to claim 1, wherein the shield material spaced-downwardly from the source comprises an end cap having one of tungsten or carbide.

5. The gauge according to claim 1, wherein an actuator is provided for translating the source from the shielded position to the measuring position.

6. The gauge according to claim 5, wherein the actuator is biased in a locked position in which the source is in the shielded position.

7. The gauge according to claim 6, wherein the actuator remains biased in the locked position unless unlocked by an operator.

8. The gauge according to claim 7, further comprising an electronic access module that must be activated in order to advance the actuator from the locked position to the unlocked position.

9. The gauge according to claim 8, further comprising an electromechanical source rod lock in communication with the electronic access module.

10. The gauge according to claim 1, further including an accelerometer for measuring shock or stress to the gauge.

11. The gauge according to claim 1, wherein the shield material positioned-downwardly from the source is fixedly secured thereto.

12. The gauge according to claim 1, further including an orientation detector for determining the orientation of the gauge.

13. The gauge according to claim 12, wherein, when the orientation detector determines that the gauge is not generally horizontal, a control module directs an electromechanical lock to lock the source into the shielded position.

14. A neutron source for use in determining one or more characteristics of a construction material, the source comprising a source shield on the top thereof and a shield material fixedly secured on the bottom thereof.

15. A gauge comprising:
    a detector; and
    a source having a shield fixedly secured to the top and bottom thereof, and being further encapsulated around a periphery thereof when in a shield position and configured such that the source is not shielded about a periphery thereof when in a measuring position,
    wherein the gauge defines a failure zone about a bottom thereof, such that in a failure where a bottom portion of the gauge separates from a remainder of the gauge, the source remains shielded.

* * * * *